United States Patent [19]
Bailey et al.

[11] Patent Number: 5,462,551
[45] Date of Patent: Oct. 31, 1995

[54] KNEE POSITIONER

[75] Inventors: James R. Bailey, Plainville; G. David Hood, Terryville; Alan A. Wasley, Southington, all of Conn.

[73] Assignee: Innovative Medical Products Inc., Plainville, Conn.

[21] Appl. No.: 222,591

[22] Filed: Apr. 4, 1994

[51] Int. Cl.[6] .................................................. A61B 17/00
[52] U.S. Cl. .................................................. 606/88
[58] Field of Search .................................... 606/88, 1, 130

[56] References Cited

U.S. PATENT DOCUMENTS

| | | | |
|---|---|---|---|
| 2,697,433 | 12/1954 | Zehnder | 606/130 |
| 4,136,858 | 1/1979 | Petersen | 269/328 |
| 4,615,516 | 10/1986 | Stulberg et al. | |
| 4,805,615 | 2/1989 | Carol | 606/130 |

FOREIGN PATENT DOCUMENTS 293760 12/1988 European Pat. Off. .................... 606/1

*Primary Examiner*—Tamara L. Graysay

[57] ABSTRACT

Apparatus for adjustably positioning human joints such as knees for surgical operating procedures having a rigid frame releasably attachable to an operating table or the like, which frame is provided with one or more rods to moveably support a carriage that can be releasably locked in position and which adjustably supports a boot or the like which can be releasably locked in position on the carriage.

2 Claims, 3 Drawing Sheets

KNEE POSITIONER

FIELD OF INVENTION

This invention relates to apparatus of the type used for the positive positioning of hands, feet, knees, etc., for surgical and other medical activities and the preferred embodiment has particular utility in the positioning of the human knee for surgery including such procedures as total knee replacement, intra-medullary rodding, tibial plateau fractures, and supra-condylar fractures in which the knee must be maintained in the selected optimum position.

BACKGROUND OF THE INVENTION

Limb surgery on the human body including knees, knee replacement, fracture repair, as well as similar hand, foot, and ankle surgery require that the joint or limb to be operated upon to be precisely and predictably positioned during such surgery. Optimum positioning requires a large range of positive positioning adjustments to be easily available so that the limb or joint to be treated is initially positioned and thereafter maintained in the desired position. Not only must such selected position be maintainable but also it is very important and often necessary that the limb be released and repositioned on demand during the course of the procedure to ensure optimum access thereby to require a variety of angular relationships for effective surgery.

OBJECTS OF THE INVENTION

It is therefore a primary object of the present invention to provide reliable support for a skeletal joint, such as a knee, during surgery which support apparatus provides a virtually unlimited range of positional adjustments both before and during the surgery as well as for diagnostic motion range testing.

It is a further object of this invention to provide surgical apparatus that is reliable safe, and durable in operation, easily maintained and sterilized, and easy for the surgeon to use during the actual operating procedure.

It is a still further object of the invention to provide apparatus which is easily adjustable by the surgeon or surgical assistant during the operation to obtain optimum positioning with minimum trauma to the patient.

It is yet a further object of the invention to provide apparatus which can be fabricated from exceedingly durable materials with a structure that is easily used and totally sterilized for use under operating room conditions.

Other objects will be in part obvious and in pan pointed out more in detail hereinafter.

SUMMARY OF THE INVENTION

In accordance with a primary embodiment of this invention, at least one elongated rod supports a carriage having a lockable and adjustable ball and socket joint to support a foot holder, knee or other limb support, the position of the carriage being adjustable along the length of the rod and easily lockable in position with a reliable fastener. The rod and its support structure being conventionally and adjustably attached to an operating table.

In accordance with a further embodiment of the invention, a pair of rails are supported on a frame which is attachable to an operating table of the like, which double rail system supports a carriage mounted on suitable beatings for selective movement back and forth along the length of the rails. As with the aforementioned embodiment, a ball and socket support for a foot hold is provided.

A better understanding of the invention will be obtained from the following detailed description and accompanying drawings of illustrative applications of the invention.

DESCRIPTION OF THE PREFERRED EMBODIMENT

Figure 1:
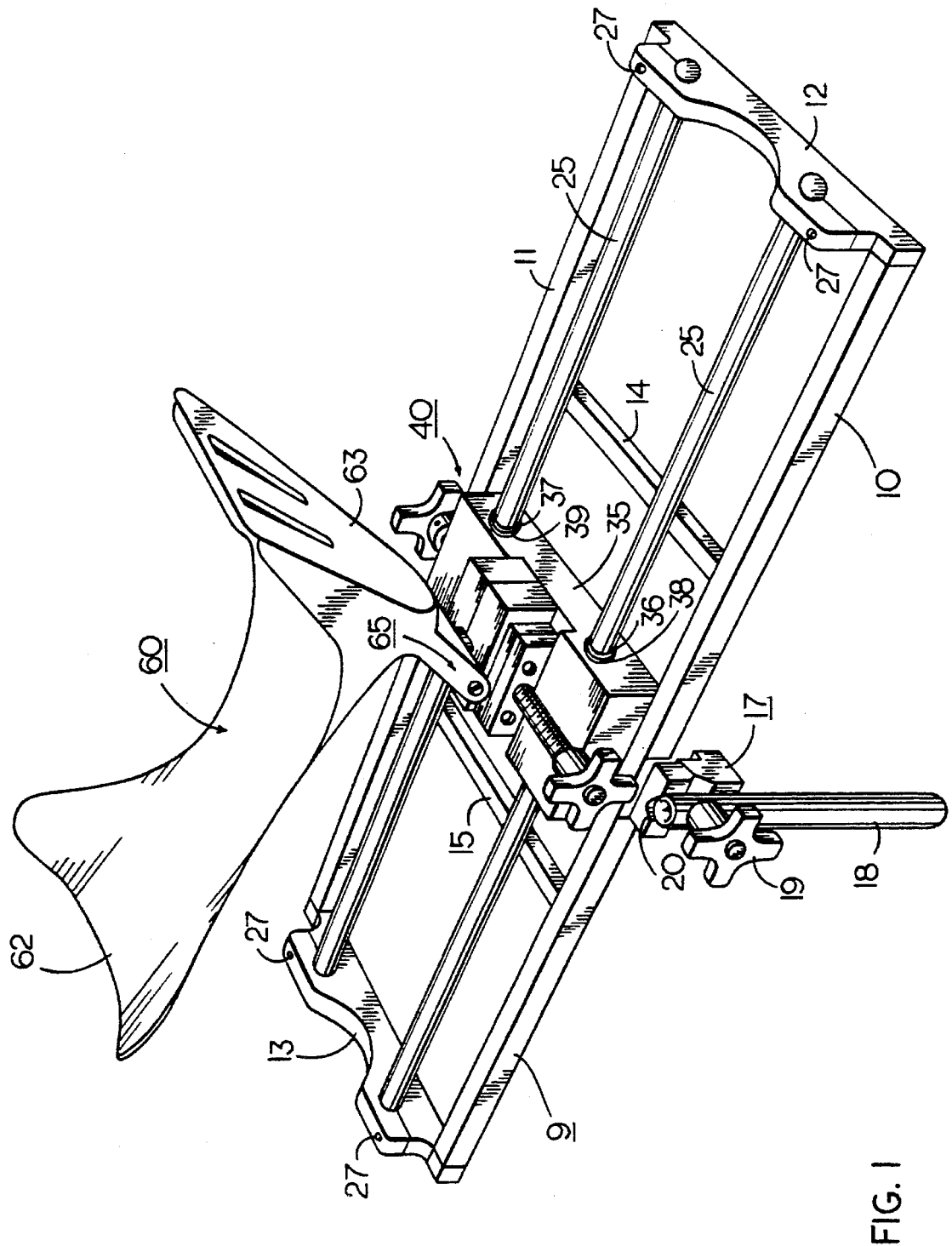
FIG. 1 is a perspective view of a preferred embodiment of the present invention.

Turning now to the drawings particularly to FIG. 1, it is seen that a preferred embodiment of the invention generally comprises a frame 9 generally including a side frame 10 and side frame 11 which are secured to end frame 12 and end frame 13 so as to define a rigid rectangular structure with the frames kept in generally parallel rigid relationship by cross members 14 and 15 secured thereto. Because the frame is intended for use in an operating room environment, the side and end frame members as well as the cross members are most commonly formed from stainless steel.

Frame 9 defines a flat structure with the side frame members 10, 11, and end frame members in 12 and 13 substantially coplaner relationship with frame 9 being attached to a suitable operating table by the mounting clamp generally designated 17 which generally comprises a rod 18, adjusting knob 19 and a clamping arrangement 20. Such a mounting clamp is basically prior art structure not forming a part of the present invention.

In the illustrated embodiment, end frame member 12 and end frame member 13 are provided with suitable apertures having longitudinally slotted sidewall portions to create, in effect, a somewhat resilient clamp such that a pair of rails 25 can be inserted into the apertures formed in end flames 12 and 13 with fasteners 27 extending through the slotted portion to permit rails 25 to be tightly clamped in position on end frame 12 and 13 and hence tightly and securely positioned within frame 9.

An alternative rail structure can be used which does depart from the spirit of this invention, namely one in which a single rail (not illustrated) having a non-circular cross section is used to support the carriage (to be described) in any desired manner. In other words, whether a pair of rails which are generally circular in cross section or a single rail which is non- circular in cross section is used, the invention remains substantially the same with the carriage positively positioned.

Carriage 35 is generally a block of metal or other suitable material provided with passageways 36 and 37 with the passageways having bearings 38 and 39 to permit easy movement of carriage 35 to the desired position along rails 25.

Figure 2:
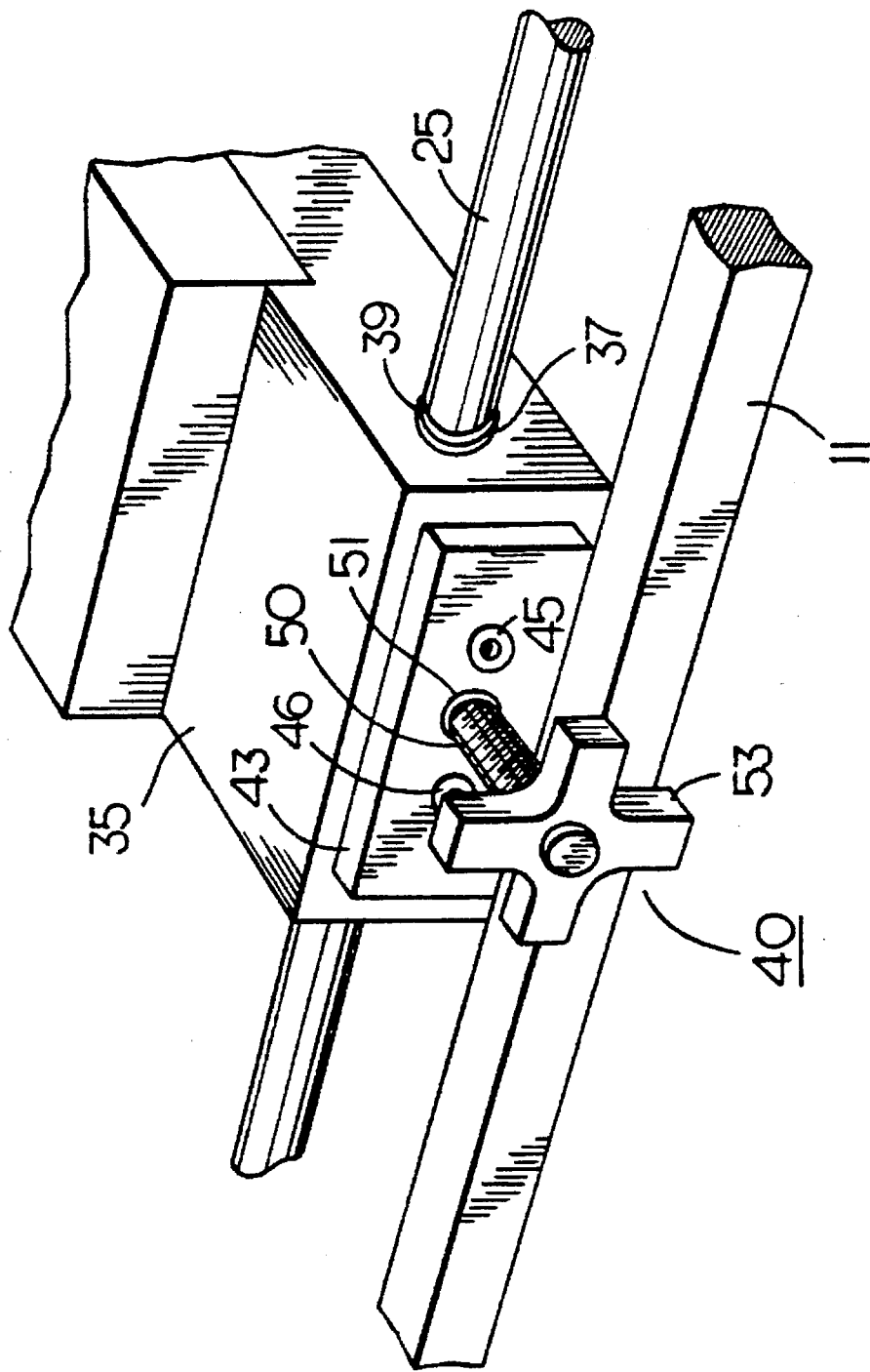
FIG. 2 is a fragmentary view of the locking means for the carriage of FIG. 3

Turning next to FIG. 2 which shows some of the details of the locking mechanism or carder lock generally designated 40 in FIG. 1, it will be seen that side frame 11 can be easily fabricated from square cross section stainless steel tubing and that rod 25 is placed within the carnage member 35 through passageway 37 with bearing 39 to facilitate movement.

In addition, carriage 35 is a plate 43 secured there to by suitable fasteners 45 and 46, which plate is provided with a threaded aperture communicating with rail 25. A threaded member 50 or positioning bolt is received in the threaded aperture 51 with knob 53 connected to the free end. By rotating knob 53, the threaded fastener is advanced to lockingly engage rail 25 and rigidly fix carriage 35 in the desired position relative to the frame 9.

Returning to FIG. 1, is seen that there is a boot like structure or holder generally designated 60 which includes an upper calf portion 62 and a heel portion 63. In accordance with the general teachings of the prior art, such a boot serves to support the extremity of the person to be operated upon. In general, the foot and ankle are rigidly fixed such as with surgical tape or other sterile means to lock the foot in position on the boot 62.

Figure 3:
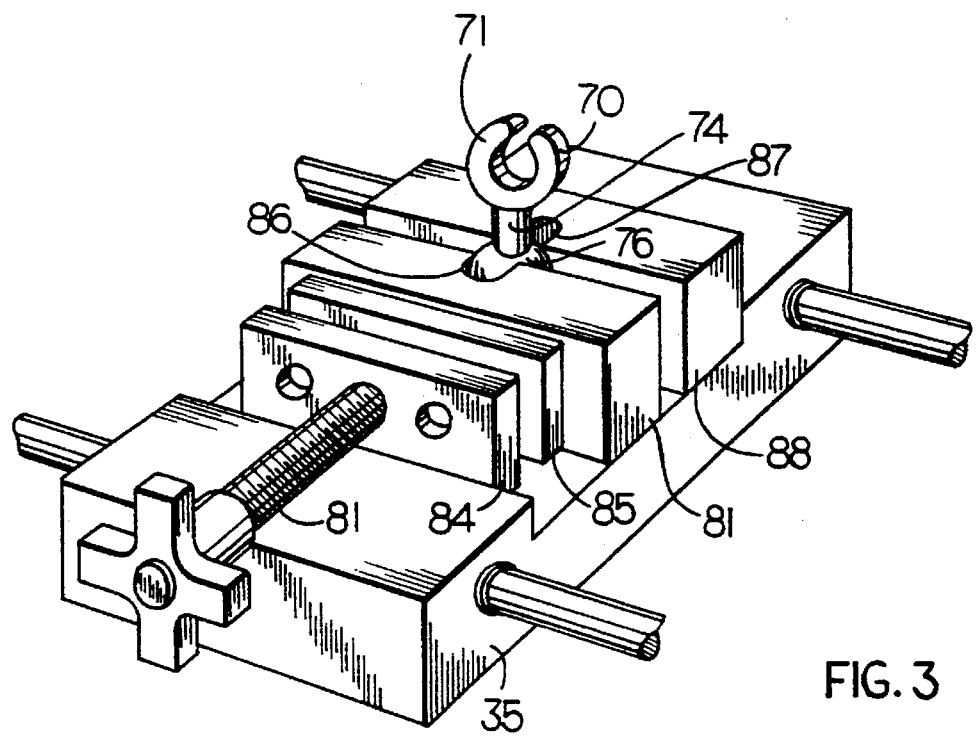
FIG. 3 is a fragmentary view of the details of the boot support of FIG. 1.
Figure 4:
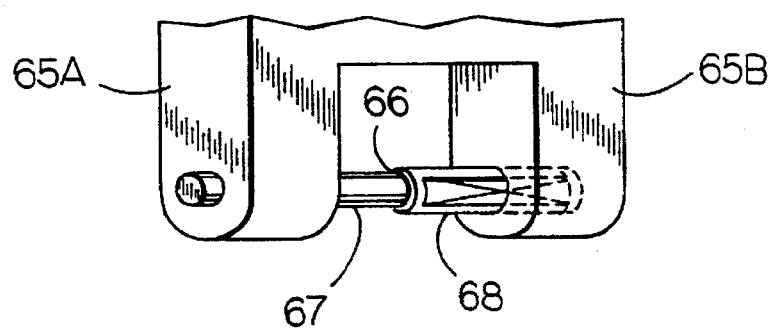
FIG. 4 is a fragmentary view of additional details of the boot support.

The support of boot 60 on carriage 35 is best seen when reviewing FIGS. 1, 3 and 4 together. Boot 60 is provided with a heel portion 65 which is a bifurcated support having two extending portions 65a and 65b each of which goes on opposite sides of the apertured support member 70. (FIG. 3) As best seen in FIG. 4, pin or rod 67 is spring loaded as at 68 in the axial direction between the bifurcated extending portion 65a and 65b and provided with a portion 66 along it's axial length (adjacent one end) of reduced diameter more or less as shown in FIG. 4. The opening 71 in support member 70 is intended to cooperate with a spring (68) loaded pin 67 with the portion 66 of reduced diameter fitting into the opening 71 such that when the pin is moved against the force of spring 68, it will clear the opening 71 in the support member 70 to permit removal of boot 60, otherwise it functions as a simple pivotal connection.

Support 70 has it's shank 74 connected to a generally ball shaped element 76 which is received between the plates 80 and 81. The plate 84 and 85 serve to mount threaded rod 81 and lock knob 88 (see FIG. 1) with the threaded member 81 connected thereto so that pressure can be applied by rotating knob 88 to fix the ball in the selected position. It should be noted that plates 80 and 81 have elongated slots 86 and 87 to permit limited tilting of shank 74 when the fastening knob is released.

Plates 84 and 85 are mounting members for threaded fastener and are arranged to retain the socket plates 80 and 81 in position in the groove provided in carriage 35. Such an arrangement permits ball 76 to be rotated through substantially 360 degrees about the vertical axis (if desired) but the stem 74 permits only limited tipping movement which will allow only for limited left and right tilting movement of boot 60; affixed thereto.

After the ankle is secured and positioned to the boot and the frame is secured to the operating table, the two adjustments, namely the carriage lock and the ball and socket lock permit limited movement of the knee joint while retaining the ankle joint fixed in position in the boot; hence the surgeon is able to easily position the knee joint as desired both before, during and after the desired surgery is conducted.

It is also to be noted that, while a foot or ankle boot is shown, clearly a supporting structure for other joints of the human body can be easily devised without departing from the essence of this invention.

Although this invention has been illustrated and described with respect to exemplary embodiments thereof, it should be understood by those skilled in the art that various changes, omissions and additions may be made without departing from the spirit and scope of the invention.

Although this invention has been illustrated and described with respect to exemplary embodiments thereof, it should be understood by those skilled in the an that various changes, omissions and additions may be made without departing from the spirit and scope of the invention.

We claim:

1. Apparatus for securing an extremity to an operating table for performing a surgical procedure comprising;

a base for securement to an operating table;

at least one elongated member supported on said base and adapted to be above the operating table;

a holder for supporting a human joint upon which a surgical procedure is to be performed, said holder being generally an L-shaped member adapted to engage and support a lower leg and foot of a patient;

a carriage supported on said base for selective movement therealong, said holder being releasably engaged with said carriage by a selectively lockable ball and socket joint for movement therewith, and releasable locking means on said carriage for positioning said carriage on said at least one elongated member, said base comprises spaced end support members and said at least one elongated member comprises a pair of spaced generally parallel elongated members passing through openings in said carriage and secured at their ends to the spaced support members, said carriage thereby being supported on said pair of elongated members for sliding movement therealong.

2. Apparatus for securing an extremity to an operating table for performing a surgical procedure comprising:

a base for securement to an operating table;

at least one elongated member supported on said base and adapted to be above the operating table, said at least one elongated member comprising generally cylindrical rods;

a holder for supporting a human joint upon which a surgical procedure is to be performed, said holder being generally an L-shaped member adapted to engage and support a lower leg and foot of a patient;

a carriage supported on said base for selective movement therealong said holder being releasably engaged with said carriage by a selectively lockable ball and socket joint for movement therewith, and releasable locking means on said carriage for positioning said carriage on said at least one elongated member;

said holder being releasably engaged with said carriage by a selectively lockable ball and socket joint for movement therewith, said ball and socket joint secured to and mounted between said carriage and said holder to permit rotary support movement there of the mounting of said ball and socket joint permitting limited movement of said holder, said lockable ball and socket joint includes an eye having an opening in the loop of the eye and a pin extending through the loop of the eye with a flat on the pin which will pass through the opening in the loop of the eye.

* * * * *